United States Patent
Chen et al.

(10) Patent No.: US 11,529,385 B2
(45) Date of Patent: *Dec. 20, 2022

(54) LYCIUM BARBARUM EXTRACTS, RESULTING COMPOSITIONS, METHODS OF MAKING AND METHODS OF USING THE SAME

(71) Applicant: Institute of Biophysics, Chinese Academy of Sciences, Beijing (CN)

(72) Inventors: Chang Chen, Beijing (CN); Jiao Meng, Beijing (CN); Zhenyu Lv, Beijing (CN); Chuanxin Sun, Beijing (CN); Xinhua Qiao, Beijing (CN)

(73) Assignee: Institute of Biophysics, Chinese Academy of Sciences, Beijing (CN)

( * ) Notice: Subject to any disclaimer, the term of this patent is extended or adjusted under 35 U.S.C. 154(b) by 6 days.

This patent is subject to a terminal disclaimer.

(21) Appl. No.: 17/411,692

(22) Filed: Aug. 25, 2021

(65) Prior Publication Data

US 2022/0072079 A1 Mar. 10, 2022

Related U.S. Application Data

(63) Continuation of application No. 17/137,805, filed on Dec. 30, 2020, now Pat. No. 11,135,260.

(60) Provisional application No. 62/958,503, filed on Jan. 8, 2020.

(51) Int. Cl.
| | |
|---|---|
| *A61K 36/00* | (2006.01) |
| *A61K 36/815* | (2006.01) |
| *A23L 33/00* | (2016.01) |
| *A61K 45/06* | (2006.01) |
| *A61P 21/06* | (2006.01) |
| *A23L 33/105* | (2016.01) |

(52) U.S. Cl.
CPC .......... *A61K 36/815* (2013.01); *A23L 33/105* (2016.08); *A23L 33/40* (2016.08); *A61K 45/06* (2013.01); *A61P 21/06* (2018.01); *A23V 2002/00* (2013.01); *A61K 2236/31* (2013.01); *A61K 2236/51* (2013.01); *A61K 2236/55* (2013.01)

(58) Field of Classification Search
CPC .............................. A61K 36/815; A61K 31/715
See application file for complete search history.

(56) References Cited

FOREIGN PATENT DOCUMENTS

| CN | 106466446 A | 3/2017 |
|---|---|---|
| CN | 109010505 A | 12/2018 |

OTHER PUBLICATIONS

Luo, Hypoglycemic and hypolipidemic effects and antioxidant activity of fruit extracts from Lycium barbarum. Life sciences, (Nov. 26, 2004) vol. 76, No. 2, pp. 137-149 (Year: 2004).*
Ahn M, Park JS, Chae S, Kim S, Moon C, Hyun JW, et al. Hepatoprotective effects of Lycium chinense Miller fruit and its constituent betaine in CCl4-induced hepatic damage in rats. Acta histochemica. 2014;116(6):1104-12.
Cheng J, Zhou ZW, Sheng HP, He LJ, Fan XW, He ZX, et al. An evidence-based update on the pharmacological activities and possible molecular targets of Lycium barbarum polysaccharides. Drug design, development and therapy. 2015;9:33-78.
Ha KT, Yoon SJ, Choi DY, Kim DW, Kim JK, Kim CH. Protective effect of Lycium chinense fruit on carbon tetrachloride-induced hepatotoxicity. Journal of ethnopharmacology. 2005;96(3):529-35.
Jia L, Li W, Li J, Li Y, Song H, Luan Y, et al. Lycium barbarum polysaccharide attenuates high-fat diet-induced hepatic steatosis by up-regulating SIRT1 expression and deacetylase activity. Scientific reports. 2016;6:36209.
Lin D, He H, Ji H, Willis J, Willard L, Jiang Y, et al. Wolfberries potentiate mitophagy and enhance mitochondrial biogenesis leading to prevention of hepatic steatosis in obese mice: the role of AMP-activated protein kinase α2 subunit. Molecular nutrition & food research. 2014;58(5):1005-15.
Luo Q, Cai Y, Yan J, Sun M, Corke H. Hypoglycemic and hypolipidemic effects and antioxidant activity of fruit extracts from Lycium barbarum. Life sciences. 2004;76(2):137-49.
Ma J, Meng X, Kang SY, Zhang J, Jung HW, Park YK. Regulatory effects of the fruit extract of Lycium chinense and its active compound, betaine, on muscle differentiation and mitochondrial biogenesis in C2C12 cells. Biomedicine & pharmacotherapy = Biomedecine & pharmacotherapie. 2019;118:109297.
Yu H, Wark L, Ji H, Willard L, Jaing Y, Han J, et al. Dietary wolfberry upregulates carotenoid metabolic genes and enhances mitochondrial biogenesis in the retina of db/db diabetic mice. Molecular nutrition & food research. 2013;57(7): 1158-69.

* cited by examiner

*Primary Examiner* — Qiuwen Mi
(74) *Attorney, Agent, or Firm* — Duane Morris LLP

(57) ABSTRACT

A composition is provided for promoting skeletal muscle oxidative muscle fiber generation. The composition comprises a *Lycium barbarum* water extract. The *Lycium barbarum* extract comprises polysaccharide, *Lycium barbarum* flavone, carotenoid, polyphenol, and *Lycium barbarum* pigment. The composition may further comprise one or more pharmaceutically acceptable excipients selected from such as a solvent, a co-solvent, an emulsifier, a preservative, a buffer, a protein powder, or a combination thereof. The composition may be used as medicine, functional product, or food supplement.

17 Claims, 22 Drawing Sheets

LYCIUM BARBARUM EXTRACTS, RESULTING COMPOSITIONS, METHODS OF MAKING AND METHODS OF USING THE SAME

PRIORITY CLAIM AND CROSS-REFERENCE

This application is a continuation of U.S. application Ser. No. 17/137,805, filed Dec. 30, 2020, which claims the benefit of U.S. Provisional Application No. 62/958,503, filed Jan. 8, 2020, which applications are expressly incorporated by reference herein in their entirety.

FIELD OF THE INVENTION

The disclosure relates to generally a composition having pharmaceutical or functional properties, comprising ingredients derived from a berry. More particularly, the disclosed subject matter relates to a *Lycium barbarum* extract, a resulting composition, methods of making the same, and methods of using the same, for example, as pharmaceutical compositions, functional compositions, and dietary supplements.

BACKGROUND

Skeletal muscle is the most abundant tissue in mammal's body, accounting for approximately 40-50% of the body mass. In addition to its primary role in posture and movement, skeletal muscle is also an extremely important metabolic organ in maintaining normal whole-body energy homeostasis.

Skeletal muscle is composed of distinct muscle fiber subtypes defined by myosin heavy chain (MyHC) isoforms and metabolic activity. Different muscle fiber subtypes differentially impact muscle metabolism and function. In mammals, skeletal muscle fibers are classified as type I (slow oxidative muscle fibers), type IIa (fast oxidative muscle fibers), type IIx/d (intermediate muscle fibers), and type IIb (fast glycolytic muscle fibers). Type I and type IIA are rich in mitochondria and myoglobin, and have high oxidative capacity and good endurance. In contrast, type IIB has lower endurance and less mitochondria and generate ATP primarily through glycolysis. The types and composition of muscle fibers directly affect the skeletal muscle fitness and the body's energy metabolism. Many diseases, such as muscle atrophy, diabetes, obesity, liver metabolism disorder and aging, are closely related to the muscle fiber types and energy metabolism.

Exercise is effective in improving muscle endurance and performance. It can significantly increase the proportion of slow oxidative fibers, and enhance mitochondrial biogenesis. Although how exercise promotes muscle fitness remains unclear, many studies have found that some signal molecules are involved in this process. Exercise can increase the level of AMP and NAD+ to activate the metabolic sensors AMPK (AMP-activated protein kinase) and SIRT1 (Sirtuin 1), then activate PGC1 by post-translational modifications. PGC1α/β function as transcription co-activators of the nuclear receptor PPARδ (peroxisome proliferator-activated receptor δ) and ERRα/γ (estrogen-related receptor α/γ), which have been identified that contribute to exercise-induced muscle fiber type switching and endurance.

In consideration of the benefic effects of exercise on skeletal muscle fitness, some muscle-targeted "exercise mimetics" drugs were begun to be developed. These compounds mimic exercise by activating some of the key regulators involved in the metabolic remodeling of skeletal muscle, such as AMPK activator, Sirt1 activator, or PPAR ligand. Although the synthetic exercise mimetics have the potential to improve the muscle fitness and endurance, the safety and health of the drug must be considered.

SUMMARY

The present disclosure provides a *Lycium barbarum* extract, a composition comprising such a *Lycium barbarum* extract, methods of making the same, and methods of using the same.

The invention proves that such a composition comprising a *Lycium barbarum* extract increases skeletal muscle weight, increases the proportion or content of the skeletal muscle oxidative muscle fibers, increases the aerobic metabolism level of skeletal muscles, reduces glycolysis level, increases myoglobin content, improves aerobic endurance, and provides resistance to exercise fatigue.

Through a series of experiments, the inventors found that long-term consumption of a water extract of *Lycium barbarum* significantly increases the muscle weight of mice, increases the proportion of oxidative muscle fibers, increases aerobic metabolism capacity, and improves exercise capacity. Through in vitro experiments by treating C2C12 myoblasts with the water extract of *Lycium barbarum*, it was found that the water extract of *Lycium barbarum* increases the expression of oxidative muscle fiber-related genes, increases the level of aerobic metabolism, and reduces the level of glycolysis. Further research found that activation of the ERRγ pathway is involved in mediating the important effect of the *Lycium barbarum* water extract on promoting transition of muscle fiber.

Therefore, the object of the present invention is to provide an important effect of *Lycium barbarum* water extract by increasing the ratio of oxidative muscle fibers and increasing aerobic metabolism of skeletal muscle by activating the ERRγ pathway. The *Lycium barbarum* water extract and related compositions have potential application value in at least the following six aspects: 1. The extract and the related compositions have potential application value of *Lycium barbarum* water extract in functional foods that enhance aerobic endurance exercise or functional foods that are simulated by exercise. 2. *Lycium barbarum* water extract has potential preventive and protective effects on astronaut's muscle tissue atrophy. 3. *Lycium barbarum* water extract has potential preventive and protective effects on muscle atrophy of patients with chronic bed. 4. *Lycium barbarum* water extract has potential preventive and protective effects on muscle atrophy in the elderly. 5. *Lycium barbarum* water extract has potential therapeutic effect on improving metabolic abnormalities in obese people. 6. *Lycium barbarum* water extract has potential application value in increasing the level of aerobic metabolism in athletes' skeletal muscle, improving aerobic endurance, and resisting sports fatigue.

In accordance with some embodiments, the present disclosure provides a composition for promoting skeletal muscle oxidative muscle fiber generation. The composition comprises *Lycium barbarum*, a *Lycium barbarum* water extract, or a combination thereof. In some embodiments, the composition further comprises one or more pharmaceutically acceptable excipients selected from the group consisting of a solvent, a co-solvent, an emulsifier, a preservative, a buffer, a protein powder, and a combination thereof.

In some embodiments, the composition comprises a *Lycium barbarum* water extract, and a *Lycium barbarum* water extract comprises polysaccharide, *Lycium barbarum* flavone, carotenoid, polyphenols and *Lycium barbarum* pigment. Each of these ingredients may have only one, or two or more of the same type. For example, the composition may include two or more types of polysaccharides, two or more types of *Lycium barbarum* flavones, two or more types of carotenoids, two or more types of polyphenols, and/or two or more types of *Lycium barbarum* pigments.

In some embodiments, in the *Lycium barbarum* extract, polysaccharide is present in a range of from about 10.0 wt. % to about 70.0 wt. % (e.g., about 50 wt. % to about 70 wt. %), *Lycium barbarum* flavone is a range of from about 0.1 wt. % to about 5.0 wt. %, carotenoid is a range of from about 0.1 wt. % to about 3.0 wt. %, polyphenol is a range of from about 0.1 wt. % to about 8.0 wt. %, and *Lycium barbarum* pigment is a range of from about 0.1 wt. % to about 8.0 wt. %, based on the total dry weight of the extract. The dry weight is equivalent weight corresponding to the extract in a dry powder (without water). The extract may contain other residues of a very small amount. The extract in the form of a dry powder can be mixed with water to provide an extract in the form of an aqueous solution having a selected concentration as described herein.

In some embodiments, the *Lycium barbarum* extract is in a powder form. In some embodiments, the *Lycium barbarum* extract is in an aqueous liquid form having a concentration, for example, in a range of from 0.1 g/mL to 5 g/mL. In some embodiments, the composition is a pharmaceutical composition including an effective amount of ingredients for promoting skeletal muscle oxidative muscle fiber generation, a functional composition, a type of food, or a dietary supplement. The composition may be in any suitable form, for example, tablet, drink (e.g., sports drink), candy, or snack bar.

In another aspect, the present disclosure provides a method of making the composition as described above. Such a method includes making an aqueous extract of *Lycium barbarum* by extracting *Lycium barbarum* berries in water. The method includes steps of making a *Lycium barbarum* extract. In some embodiments, the steps of making the *Lycium barbarum* extract include steps as described herein. For example, the steps of making the *Lycium barbarum* extract include: soaking dried *Lycium barbarum* berries in water, crushing the *Lycium barbarum* berries to provide a soaked berry powder, decocting the soaked berry powder in boiling water twice to obtain a decoction, distilling the decoction under vacuum after a filtration to obtain a concentrate, and lyophilizing the concentrate to obtain a dry powder as the *Lycium barbarum* extract. The method may further comprise formulating the composition by adding one or more ingredients into the aqueous or dried powder extract of *Lycium barbarum*. The method may further comprise dissolving the *Lycium barbarum* extract in water to obtain an aqueous liquid.

In another aspect, the present disclosure provides a method of using the composition as described above. Such a method includes administering or taking a suitable amount of the composition into a human subject. In some embodiments, the composition is used to increase the weight of skeletal muscle, and/or increase the proportion of skeletal muscle oxidative muscle fibers. In some embodiments, the composition may also be used to improve the level of aerobic metabolism, and/or reduce glycolysis level. In some embodiments, the composition may also be used to increase the content of myoglobin, improve exercise endurance, and/or combat sports fatigue, and/or in exercise simulation. In some embodiments, the composition is used to activate the ERRγ pathway, and/or regulate muscle fiber types by activating the ERRγ pathway.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

DETAILED DESCRIPTION

Figure 1C:
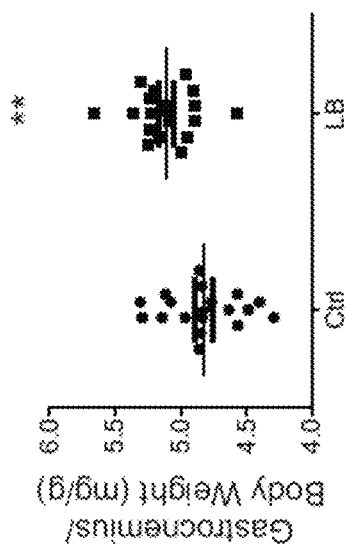
FIGS. 1B-1C show the weights of the tibialis anterior muscle and gastrocnemius muscle of the control group, and the experimental group with the *Lycium barbarum* water extract.

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure the singular forms "a," "an," and "the" include the plural reference, and reference to a particular numerical value includes at least that particular value, unless the context clearly indicates otherwise. Thus, for example, a reference to "a nano structure" or an ingredient is a reference to one or more of such structures and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

As described above, the synthetic exercise mimetics have the potential to improve the muscle fitness and endurance, but the synthetic mimetics may have the safety and health issues needed to be considered.

Therefore, discovery of natural medicine edible plants that have mimetic effects of exercise has great importance and significance.

The present disclosure provides compositions and methods related to the application of *Lycium barbarum* (LB) extract in promoting the generation of skeletal muscle oxidative muscle fibers, and belongs to the field of natural product treatment.

The present disclosure provides a composition and a method for application of *Lycium barbarum* extract in promoting skeletal muscle oxidative muscle fiber generation. In the present invention, the water extract of *Lycium barbarum* was used to administer mice. Compared with the control group, the weight of the tibialis anterior muscle and gastrocnemius muscle of the mice in the administration group significantly increased, the proportion of oxidative muscle fibers increased, and the content of myoglobin increased, aerobic metabolism capacity increased, exercise endurance capacity, and average exhaustion running distance increased by about 40%. In the in vitro experiment, C2C12 myoblasts were treated with water extract of *Lycium barbarum*. Compared with the control group, the water extract of *Lycium barbarum* can increase the expression of oxidative muscle fiber-related genes, increase the level of aerobic metabolism, and reduce the level of glycolysis. Furthermore, by interfering with the expression of ERRγ (Estrogen receptor-related receptor-γ) gene, it was proved that the water extract of *Lycium barbarum* promotes the generation of oxidative muscle fibers by activating the ERRγ pathway. The present invention proves that *Lycium barbarum* has the effect of promoting the generation of oxidative muscle fibers of skeletal muscle, and *Lycium barbarum* has the potential to be applied to sports food or exercise simulation food for enhancing aerobic endurance.

*Lycium barbarum* berries are used for extraction. In the present disclosure, *Lycium barbarum* (or *L. barbarum*) extract can be used as a dietary natural "exercise mimetic" agent for the people lacking or unable to achieve adequate physical exercise. *Lycium barbarum* extract has effect on skeletal muscle fiber type switch and energy metabolism in vitro and in vivo.

Unless expressly indicated otherwise, references to a "composition" made herein are understood to encompass a composition in any suitable form, including but not limited to a solid, a liquid, and a paste. Unless expressly indicated otherwise, references to a "water extract" or "extract" are understood to encompass an extract of *Lycium barbarum* in any suitable form, including but not limited to a solid form such as a dry powder, a paste, and a liquid form. For example, as described herein, dried berries of *Lycium barbarum* can be extracted using the method descried herein using boiling water to obtain an aqueous extract, which is dried to provide an extract in the dry powder form. The term "water extract" may refer to an extract in powder form. The dry powder is then dissolved in water to make an aqueous extract of a suitable concentration. The weight percentages of ingredients in an extract are the contents of the ingredients in an extract of dry powder form. Unless expressly indicated otherwise, a concentration of an aqueous extract is defined by the mass of a dry weight of the extract (the equivalent mass of an extract in dry powder form) and the volume of the aqueous extract. The terms "weight" and "mass" herein are used interchangeably.

In the embodiment of the present disclosure, the components of the water extract of *Lycium barbarum* mainly include water-soluble ingredients such as polysaccharides, *Lycium barbarum* flavones, carotenoids, polyphenols, and *Lycium barbarum* pigments. The *Lycium barbarum* polysaccharides may be in a range of from about 10.0 wt. % to about 70.0 wt. %, and the molecular weight may be in a range between $4.50 \times 10^3$D to $6.05 \times 10^5$D. For example, the polysaccharides may be in a range of from about 20.0 wt. % to about 70.0 wt. %, from about 30.0 wt. % to about 70.0 wt. %, or from about 40.0 wt. % to about 70.0 wt. %. In some embodiments, the polysaccharides is more preferably from about 50.0 wt. % to about 70.0 wt. %. In some embodiments, the content of arabinose, galacturonic acid and galactose is not less than 60% in sugar composition. In some embodiments, the content of polysaccharide was 54% and the molecular weight was between $6.50 \times 10^3$D to $5.05 \times 10^5$D.

In addition to polysaccharide, each other ingredient may be in a suitable range. For example, in some embodiments, *Lycium barbarum* flavone has a content in a range of from about 0.1 wt. % to about 5.0 wt. % (e.g., 0.5-5%, 1-5%, 2-5%, or 3-5%), carotenoid has a content in a range of from about 0.1 wt. % to about 3.0 wt. % (e.g., 0.2-3%, 0.5-3%, or 1-3%), polyphenol has a content in a range of from about 0.1 wt. % to about 8.0 wt. % (e.g., 0.5-8%, 1-8%, 2-8%, 4-8%, 5-8% or any other suitable range), and *Lycium barbarum* pigment has a content in a range of from about 0.1 wt. % to about 8.0 wt. % (e.g., 0.1-7%, 0.1-6%, 0.1-5%, 0.1-4%, or any other suitable range). These weight percentages are relative to the total weight of the extract in dry powder form.

In the embodiment of the present invention, the aqueous extract of *Lycium barbarum* is administered by gavage or orally, but it is not limited thereto. Any form of administration of having the composition into stomach may be suitable.

In some embodiments of the present invention, the dosage of the *Lycium barbarum* water extract is 2.5 g/Kg (the dry weight of the exemplary extract/the body weight of animals such as mice). With reference to the equivalent dose ratio between humans and animals in "Pharmacological Experiment Methodology" edited by Professor Xu Shuyun, it was calculated that this dose was equivalent to 19.39 g/70 Kg in humans. The ratio of a dosage in mice ($D_1$) to that in humans ($D_2$) is calculated based on an equation: $D_1=D_2*9.023$. The administered dose does not limit the scope of the invention in any way. For example, the dosage may be in a range of from about 10.0 g/70 Kg to about 40.0 g/70 Kg. In these dosages, the mass in grams refers to the equivalent dry weight of the corresponding extract, and the mass in Kg refers to body weight of a human subject.

The water extract of *Lycium barbarum* provided by the invention is homologous in medicine and food, and can be used as a healthy food. Food or health food preparations are not particularly limited. For example, it can be made into tablets, drinks, candies, and the like. Each food preparation may include other ingredients used in the art in addition to the *Lycium barbarum* water extract. The other ingredients can be selected by those skilled in the art considering the specific formulation or purpose used.

In some embodiments, the composition is a food or health product including sports drinks, protein powder and the like.

The features and effects of the present invention will be explained through Preparation Examples and Test Examples. However, the following preparation examples and test examples are for illustration only, and do not limit the scope of the present invention.

EXAMPLES

Unless indicated otherwise, the water used herein is double-distilled water (pH=7).

All animal experiments with mice were performed in C57BL/6. The care and handling of animals was performed in accordance with the guidelines of the Animal Ethics Committee.

1. Preparation of *Lycium barbarum* Extract:

*Lycium barbarum* extract was prepared in the following general procedures: *Lycium barbarum* berries were cultivated in and obtained from Zhongning County, Yinchuan, Ningxia, China. The dried berries were soaked in double-distilled water (pH=7) at room temperature for 2 hours after being washed 3-5 times, then crushed. The soaked berries powder were added 5-8 times neutral water, mixed uniformly and decocted at a boiling temperature twice, with a period of time for decocting of 2.0 h and 1.5 h, respectively. The combined concentrated decoctions were filtered by a hollow fiber membrane. The above filtrates were merged and evaporated under a vacuum at 30-55° C. to remove water and obtain the concentrate. The resulting concentrate was lyophilized into a powder and stored in a desiccator, and it was used for the following experiments at suitable concentration.

In the experiments, an exemplary resulting *Lycium barbarum* extract (Experimental Example 1) was used. Such exemplary extract is an aqueous extract solution, and has a concentration of 1 g/mL (the equivalent mass of dry powder or dry weight of the extract/the volume of the extract). This concentration is for illustration only. The aqueous extract may be adjusted to have any suitable concentration, for example, in a range of from about 0.1 g/mL to 5 g/mL (the dry weight of the exemplary extract/the volume of extract). Such an aqueous extract may be diluted for administration in some embodiments. The aqueous extract may be further diluted for experiments with cells.

The *Lycium barbarum* extracts provided in the present disclosure include mainly water-soluble *Lycium barbarum* polysaccharides, *Lycium barbarum* flavonoids, carotenoids, polyphenols, and pigment. In the exemplary extract used, polysaccharide is present in a range of from about 50.0 wt. % to about 70.0 wt. % (e.g., about 54%-56% or 54%), *Lycium barbarum* flavone is a range of from about 0.1 wt. % to about 5.0 wt. %, carotenoid is a range of from about 0.1 wt. % to about 3.0 wt. %, polyphenol is a range of from about 0.1 wt. % to about 8.0 wt. %, and *Lycium barbarum* pigment is a range of from about 0.1 wt. % to about 8.0 wt. %, based on the total equivalent weight of the extract in dry powder form.

2. Cell Culture and Treatment:

Mouse C2C12 cells were cultured in growth medium consisting of Dulbecco's modified Eagle's medium (DMEM; Gibco) supplemented with 4.5 g/liter glucose, 10% fetal bovine serum (FBS), 1% antibiotic/antimycotic, and 1% gentamycin at 37° C. in a 5% $CO_2$ atmosphere.

3. Exercise Capacity by Treadmill Test:

Treadmill Test: The treadmill test was performed using an Exer3/6 (Columbus Instruments). Mice were acclimated to treadmill running three times (every other day) before the test was performed. Mice ran on the treadmill at 15° downhill, starting at a speed of 10 m/min. After 3 min, the speed was increased by 2 m/min to a final speed of 30 m/min. Exhaustion was defined as the inability of the animal to remain on the treadmill despite electrical prodding.

4. Measurement of Lactate Release:

The amount of lactate in the serum of the mice was determined using a commercial kit. The detection principle is that LDH catalyzes the dehydrogenation of lactic acid to produce pyruvic acid with NAD+ as the hydrogen acceptor, so that NAD+ can be converted into NADH. The NBT was reduced to purple color by PMS dehydrogenation, and the absorbance of the color was linear with the content of lactic acid at 530 nm.

5. Immunofluorescence Staining of Frozen Sections:

Prior to immunofluorescent staining, the frozen sections of muscle were fixed in cold acetone (−20° C. precooling) for 20 min, washed three times with PBS, and permeabilized with 0.2% Triton X-100/PBS (PB ST) for 10 min. After washing with PBS, the cells were blocked by incubating with 5% BSA at room temperature for 2 h. Cells were immunostained by incubating with the first antibody overnight at 4° C. After washing, immunoreactive proteins were visualized following incubation with a fluorescein isothiocyanate (FITC)-conjugated goat anti-rabbit IgG antibody (Zhongshanjinqiao Corp.). Nuclei were stained with Hoechst (Santa Cruz). The cells were then observed using a confocal laserscanning microscope (LSM750) (Carl Zeiss).

6. Real-Time qPCR:

Total RNA was extracted using TRIzol reagent according to the manufacturer's (Invitrogen) protocol. RNA samples were then reverse transcribed using M-MuLV reverse transcriptase, and mRNA levels were measured by performing RT-qPCR on a 7500 Real-Time PCR System (Applied Biosystems). The samples were heated to 95° C. for 2 min and subjected to 40 cycles of amplification (1 min at 94° C., 1 min at 58° C., and 1 min at 72° C.), followed by 10 min at 72° C. for the final extension.

7. Western Blotting:

Cells were lysed in radio immunoprecipitation assay (RIPA) buffer (150 mM NaCl, 1% NP-40, 0.5% DOC, 0.1% SDS, 50 mM Tris, pH 7.4, 5 mM EDTA and protease inhibitor cocktail solution (Roche)), and lysates were cleared by centrifugation. For each sample, 40 mg of protein was separated by sodium dodecyl sulfate-polyacrylamide gel electrophoresis (SDS-PAGE) and transferred to a PVDF membrane. Membranes were blocked in 5% skim milk powder in TBST (0.1% Tween-20) for 1 h and incubated with the following primary antibodies overnight at 4° C.: anti-iNOS (1:500, Santa Cruz); anti-p-ERK, anti-ERK, anti-p-AKT, anti-AKT, anti-p-AMPKα/β, and anti-AMPKα/β (1:1000, Cell Signaling); anti-HIF-1α (1:200, Santa Cruz); anti-Nrf2 (1:200, Santa Cruz); anti-HSP60, anti-HSP70, and anti-HSP90 (1:500, Santa Cruz); anti-LC3 (1:1000, MBL) or anti-actin (1:2000, Sungene Biotech). After washing in TBST, the membranes were incubated for 1 h at room temperature with a horseradish peroxidase (HRP)-conjugated secondary antibody (Zhongshanjinqiao Corp.) at a 1:2000 dilution and then washed three times with TBST. Each membrane was placed into ECL solution (Thermo), and signals were subsequently detected using a Molecular Imager ChemiDoc XRS+(BioRad) and analyzed using Image Lab 4.0.1.

8. Metabolic Measurement:

Metabolic measurements were obtained by using an Oxymax Lab Animal Monitoring System (Columbus Instruments, Columbus, Ohio). The system was calibrated against a standard gas mixture to measure $O_2$ consumed ($VO_2$, ml/kg/h) and $CO_2$ generated ($VCO_2$, ml/kg/h). These measurements were taken on animals that had received *Lycium barbarum* for 2 months. The first 12 h were a period of adaptation for the animals, and then metabolic rate ($VO_2$) and food intake were evaluated for a 24-h period. Energy expenditure (or heat production) was calculated as the product of the calorific value of oxygen (3.815_1.232_respiratory quotient) and the volume of $O_2$ consumed.

9. XF24 Oxygen Consumption Assay and Oxygen Consumption Rate:

Oxygen consumption was measured using the XF24 Extracellular Flux Analyser from Seahorse Bioscience. For this, 2 h before the analysis, control, overexpressing C2C12 myoblasts on 24-well XF24 V28 cell culture microplate (Seahorse Bioscience) were pretreated compound C. One hour before the experiment, cells were washed and incubated in 630 ml of non-buffered (without sodium carbonate) DMEM (4.5 g/L glucose) pH 7.4 at 37° C. in a non-$CO_2$ incubator. Five replicates per cell type were included in the experiment, and four wells evenly distributed within the plate were used for correction of temperature variations. During the time course of the experiment, oxygen concentration was measured over time periods of 2 min at 6-min intervals, consisting of a 2 min of mixing period and a 4 min waiting period. OCR over the 2 min measurement period was calculated using the Fixed Delta technique for determining the slope.

10. ATP Production Assay/Statistical Analysis

The amount of ATP production from the cells was determined using a commercial kit (Beyotime Biotechnology, Shanghai, China). The principle of the experiment is based on the fact that ATP is needed to provide energy when firefly luciferase (luciferase) catalyzes the production of fluorescence. When both fluorescein enzyme and fluorescein are excessive, the production of fluorescence is directly proportional to the concentration of ATP in a certain concentration range. In this way, ATP concentration in solution can be detected with high sensitivity. The results are presented as the mean±standard error of the mean (SEM) of at least 3 independent experiments. The statistical significance of the difference between two means was calculated using Student's t-test, and differences between control and treated groups were calculated by performing a 2-way ANOVA analysis. For all analyses, $p<0.05$ was considered statistically significant, and significance levels are indicated as follows: *, $p<0.001$; , $p<0.01$; *, $p<0.05$.

Experimental Example 2: *Lycium barbarum* Extracts (LB) Increases the Weight of Skeletal Muscles and Enhance Exercise Capacity Male C57BL/6 mice of about 8 weeks of age purchased from Weitong Lihua Company were randomly divided into a control group and a *Lycium barbarum* administration group. In the *Lycium barbarum* group ("LB"), *Lycium barbarum* extract was administered by gavage to 2.5 g/kg daily, and physiological saline was used as a control group ("Ctrl"). The mice were given *Lycium barbarum* for 4 months. After the *Lycium barbarum* extract was administered to the stomach, the mice in the control group and the *Lycium barbarum* group were weighed respectively. The mice were anesthetized with ether, blood was taken, then the neck was sacrificed, and the anterior tibialis and gastrocnemius muscles of the legs of the mice were dissected and weighted.

Figure 1B:
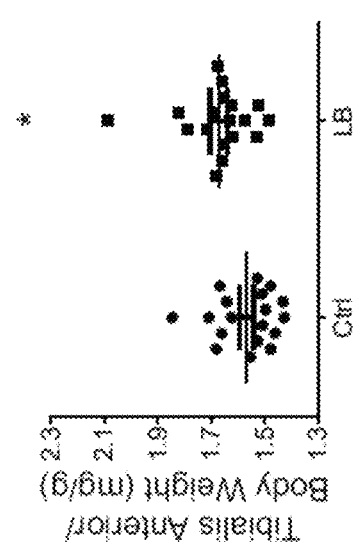
Figure 1A:
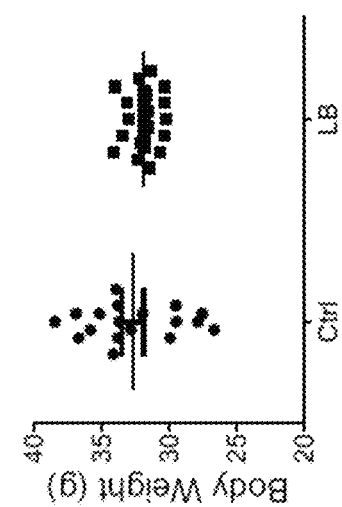
FIG. 1A shows the body weights of the mice in the control group, and the mice in the experimental group administrated with the *Lycium barbarum* (LB) water extract.

As shown in FIGS. 1A-1C, the water extract of *Lycium barbarum* had no significant change in mouse weight (FIG. 1A), but it could significantly increase the weight of the tibialis anterior and gastrocnemius muscles of mice (FIGS. 1B-1C).

The running experiment was used to test whether the extract of *Lycium barbarum* could improve the exercise ability of mice. The mouse running instrument was set to rotate the conveyor belt, that is, the running speed of the mouse and the intensity of electrical stimulation. The inclination of the running platform of the mouse was set to 15 degrees. The mouse was placed in the running channel, first equilibrated for 3 minutes at a speed of 10 m/min, then accelerated to 30 m/min at an acceleration of 2 m/min within 10 minutes, and then moved at a uniform speed at this speed. The mouse's continuous activity was taken in the electric shock zone or the second half of the running platform connected to the electric shock zone as the standard for the initial fatigue of the mouse. If the mouse stayed in the electric shock zone under the 2.5 mA current stimulation, the mouse was completely fatigued. The total distance that the mice ran was recorded at the time of complete fatigue, and this was taken as the mouse's exhausted exercise capacity.

Figure 2A:
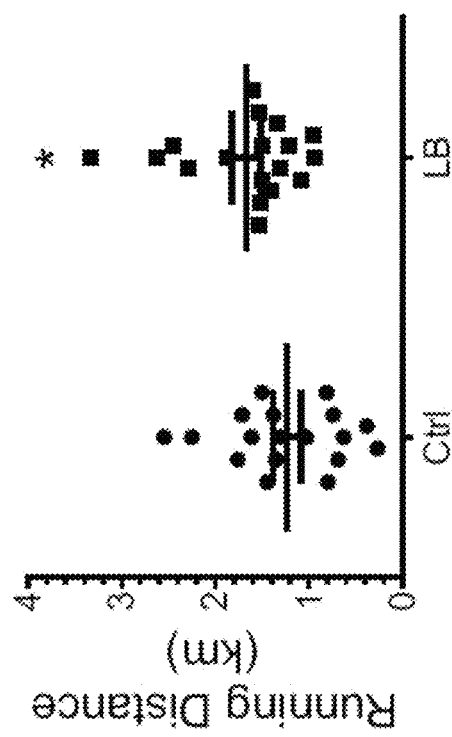
FIG. 2A shows the exhausted running distance of the mice in the control group, and the mice in the experimental group with the *Lycium barbarum* water extract.
Figure 2B:
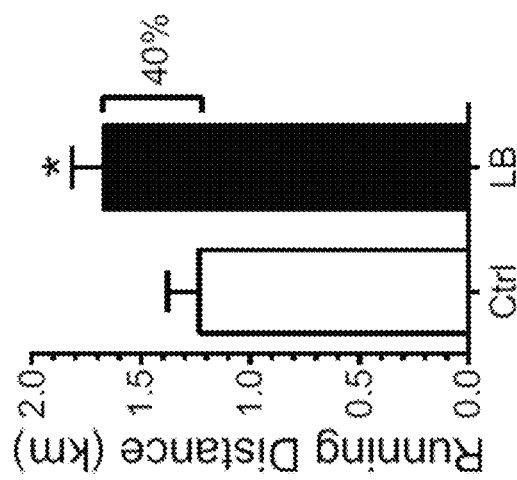
FIG. 2B is a bar graph showing the exhausted running distance of the mice in the control group, and the mice in the experimental group with the *Lycium barbarum* water extract.

As shown in FIG. 2B, water extract of *Lycium barbarum* can significantly increase the running distance of mice in exercise experiments by about 40%, which improves the exercise ability of mice. *Lycium barbarum* extracts relieve muscle fatigue and enhance endurance.

The effect of *Lycium barbarum* extracts (LB) on skeletal muscles was evaluated in male C57BL/6J mice that were administrated a dose of 2.5 g/kg/day of LB (normal saline as control) through intragastric administration for 4 months. The mice in LB group had no change of the body weight compared to the control group (FIG. 1A), but they showed obvious change in muscle mass (FIGS. 1B-1C). LB significantly increased the weight of tibialis anterior (TA) and gastronemius (GAS) (FIGS. 1B-1C).

Figure 3:
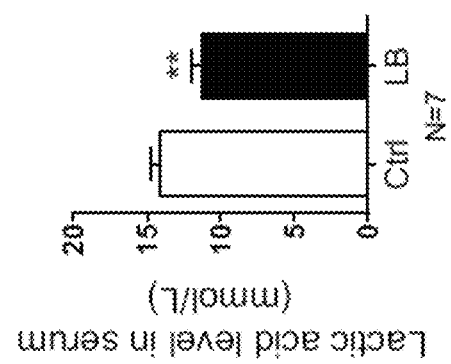
FIG. 3 shows the lactic acid content in the serum of the mice in the control group and in the experimental group with the *Lycium barbarum* water extract.
Figure 4C:
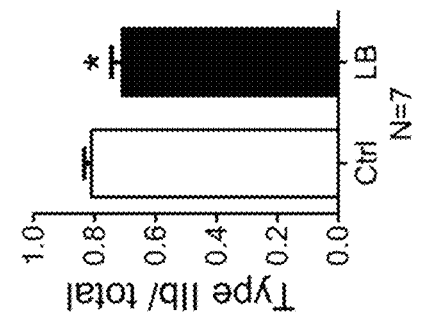
FIG. 4C shows the type IIb muscle fibers statistical results in the tibialis anterior of the mice in the control group and the experimental group with water extract of *Lycium barbarum*.
Figure 4B:
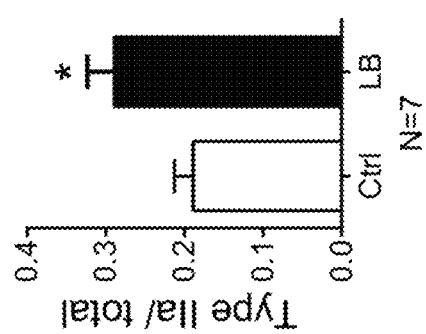
FIG. 4B shows the type IIa muscle fibers statistical results in the tibialis anterior of the mice in the control group and the experimental group with water extract of *Lycium barbarum*.
Figure 4A:
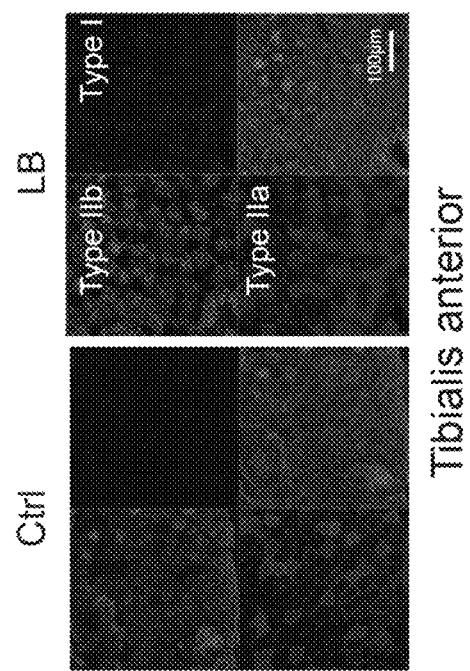
FIG. 4A shows the immunofluorescence staining results of different types of muscle fibers in the tibialis anterior of the mice in the control group and the experimental group with water extract of *Lycium barbarum*. Type I, type IIa, and IIb Type.
Figures 4D, 4E, 4F, 4G:
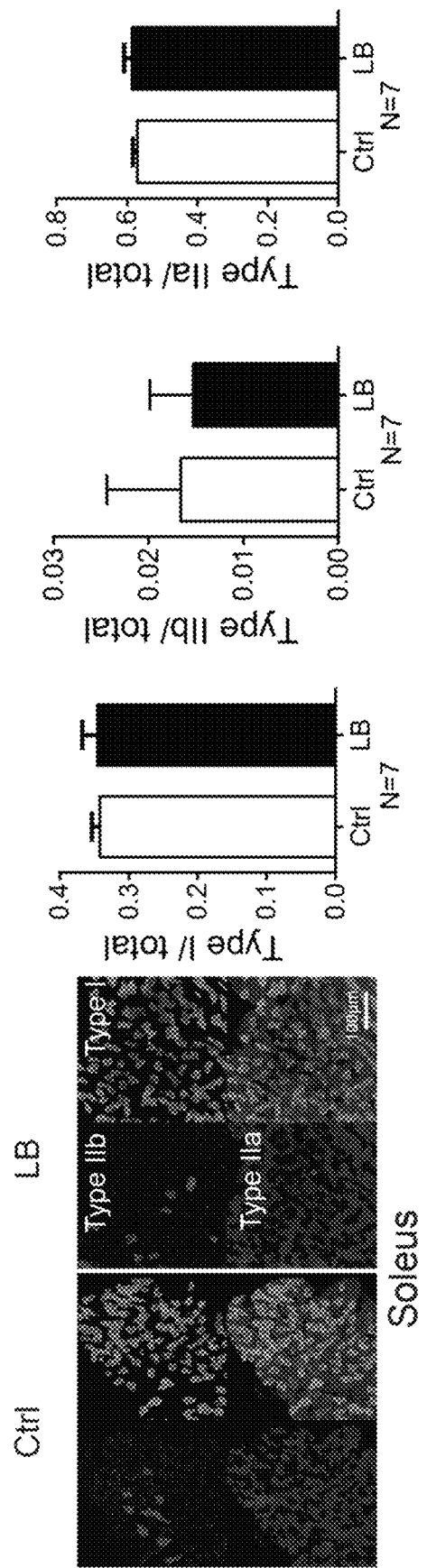
FIG. 4D shows the immunofluorescence staining results of different types of muscle fibers in the soleus muscles of the mice in the control group and the experimental group with water extract of *Lycium barbarum*. Type I, type IIa, and IIb Type.
FIG. 4E shows the type I muscle fibers statistical results in the soleus muscles of the mice in the control group and the experimental group with water extract of *Lycium barbarum*.
FIG. 4F shows the type IIb muscle fibers statistical results in the soleus muscles of the mice in the control group and the experimental group with water extract of *Lycium barbarum*.
FIG. 4G shows the type IIa muscle fibers statistical results in the soleus muscles of the mice in the control group and the experimental group with water extract of *Lycium barbarum*.

In order to investigate the effect of LB on improving muscle function, the exercise capacity of the mice was tested. The exhausting running distance of the mice in LB group is much longer than the control group (FIG. 2A). These findings suggest that endurance based on oxidative fiber type was increased by LB. Meanwhile, the decreased lactic acid level in serum also supported that LB relieved the muscle fatigue (FIG. 3). Therefore, LB feeding in mice for long time relieved the muscle fatigue and enhanced endurance, and this function may be related to the change of muscle fiber types.

Experimental Example 3: LB (*Lycium barbarum* Extract) Promoted Muscle Glycolytic-to-Oxidative Fiber Type Switch In Vivo and In Vitro To further validate the shift in muscle fiber types following LB feeding, type I (oxidative), type IIa (oxidative) and type IIb (glycolytic) fibers were stained by IF on the frozen sections of the muscles (FIGS. 4A-4G). In TA muscles, there was almost no type I fibers, the ratio of type IIa fibers was increased significantly, with corresponding the ratio of type IIb was decreased (FIGS. 4A-4C), which indicated that LB promoted glycolytic-to-oxidative fiber type switch in vivo.

Figure 5C:
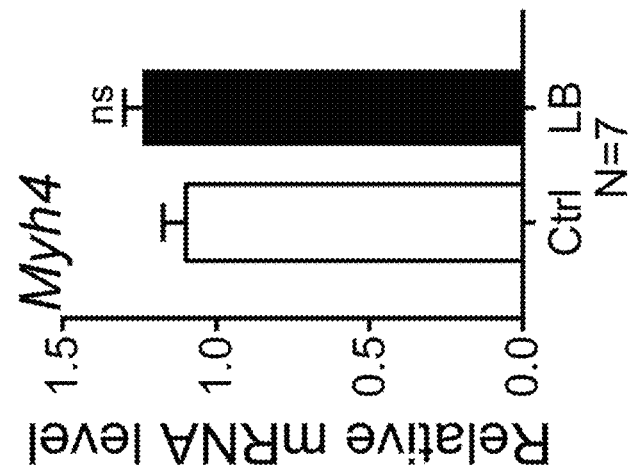
FIG. 5C shows the expression levels of myosin heavy chain isoforms 4 (Myh4) in the tibialis anterior muscles of the mice in the control group and in the experimental group with the *Lycium barbarum* water extract.
Figure 5B:
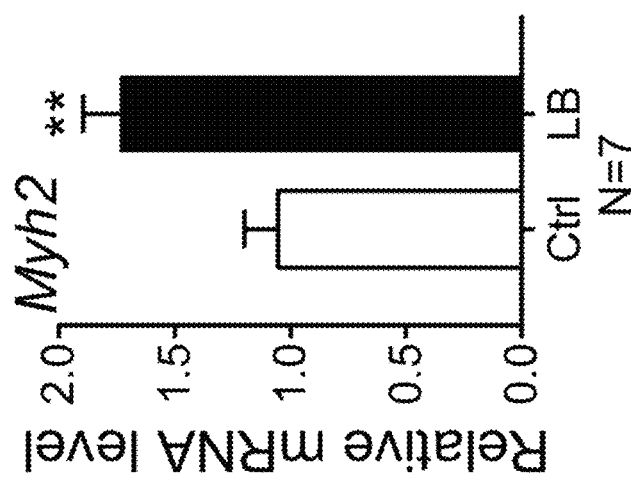
FIG. 5B shows the expression levels of myosin heavy chain isoforms 2 (Myh 2) in the tibialis anterior muscles of the mice in the control group and in the experimental group with the *Lycium barbarum* water extract.
Figure 5A:
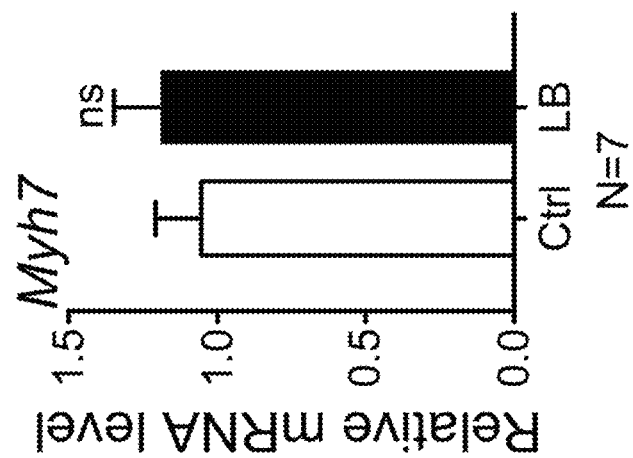
FIG. 5A shows the expression levels of myosin heavy chain isoforms 7 (Myh 7) in the tibialis anterior muscles of the mice in the control group and in the experimental group with the *Lycium barbarum* water extract.
Figure 6:
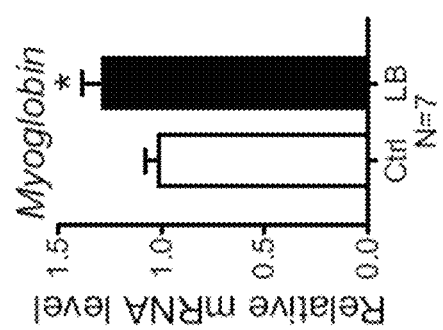
FIG. 6 shows the expression level of myoglobin in the tibialis anterior muscle of the mice in the control group and in the experimental group with the *Lycium barbarum* water extract.
Figure 7:
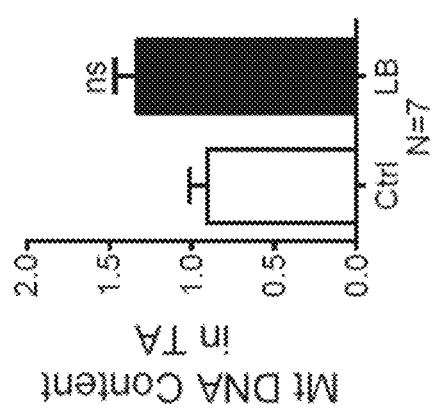
FIG. 7 shows the number of mitochondrial DNA copies in the tibialis anterior muscles of the mice in the control group and in the experimental group with water extracts of *Lycium barbarum*.
Figures 8A, 8B, 8C, 8D:
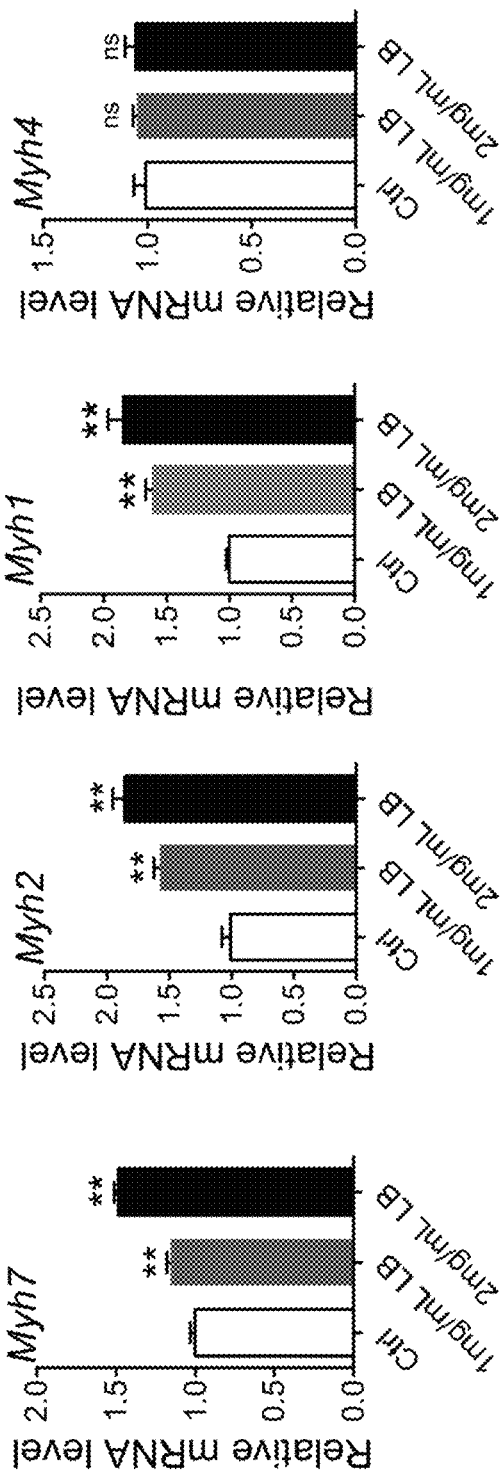
FIG. 8A shows the expression levels of muscle fiber-related gene Myh7 in the myotubes treated with the water extract of *Lycium barbarum* and those in the control group.
FIG. 8B shows the expression levels of muscle fiber-related gene Myh2 in the myotubes treated with the water extract of *Lycium barbarum* and those in the control group.
FIG. 8C shows the expression levels of muscle fiber-related gene Myh1 in the myotubes treated with the water extract of *Lycium barbarum* and those in the control group.
FIG. 8D shows the expression levels of muscle fiber-related gene Myh4 in the myotubes treated with the water extract of *Lycium barbarum* and those in the control group.

At the same time, qPCR was used to determine the expression of mRNA characteristic of type IIa and type IIb fibers. It revealed an increase in mRNA expression of Myh2, a marker of type IIa fibers (FIG. 5B), and no change in the transcript levels of Myh7 and Myh4, which are markers of type I and type IIb fibers (FIGS. 5A and 5C), respectively. Because oxidative fibers are rich in mitochondria and myoglobin, increased myoglobin expression and mtDNA content in TA muscles after LB treatment also confirmed that LB enhanced endurance through promoting glycolytic-to-oxidative fiber type switch (FIGS. 6-7). However, in soleus muscles, there was no significant change in the proportion of three types of muscle fibers due to the extremely small number of type IIb fibers (FIG. 4D-4G).

In differentiated myotube, the expression of markers of type IIa and type IIb fibers was also evaluated in vitro. Consistent with the results in vivo, the mRNA level of the markers of oxidative fiber (Myh7, Myh2, and Myh1) was induced by LB in a dose dependent manner, and the level of Myh4 had no change (FIGS. 8A-8D). Therefore, LB promoted muscle glycolytic-to-oxidative fiber type switch in vivo and in vitro.

Experimental Example 4: LB Enhanced the Oxidative Capacity In Vivo

Distinct muscle fiber subtypes are closely related to metabolic activity, type I and type IIA are rich in mitochondria and myoglobin, and have high oxidative capacity.

Figures 9A, 9B:
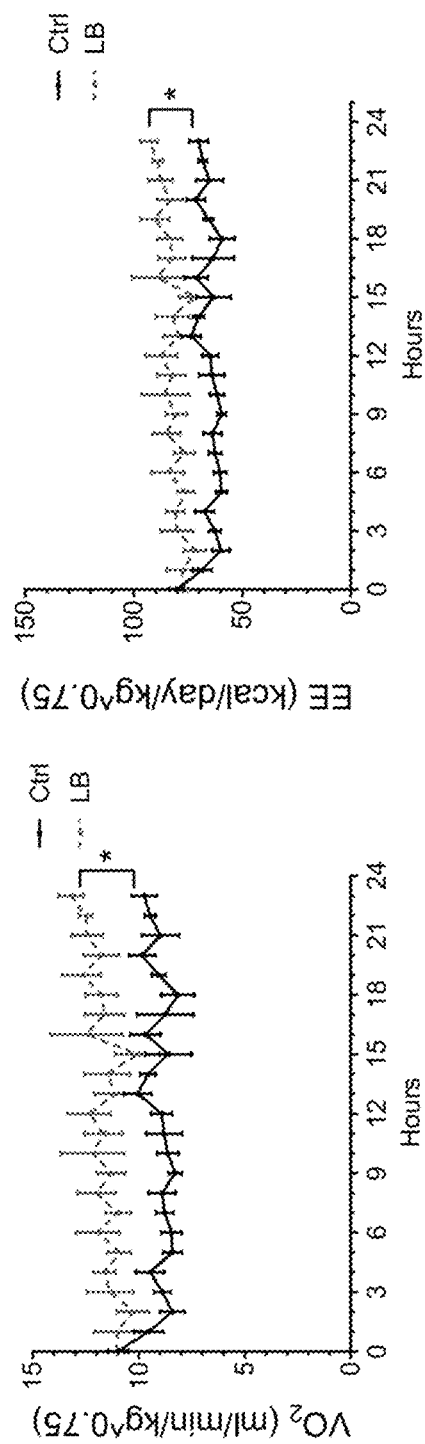
FIG. 9A shows the maximal oxygen consumption of the mice in the control group and the experimental group with the water extract of *Lycium barbarum*.
FIG. 9B shows the energy exchange rate of the mice in the control group and the experimental group with the water extract of *Lycium barbarum*.
Figures 9C, 9D:
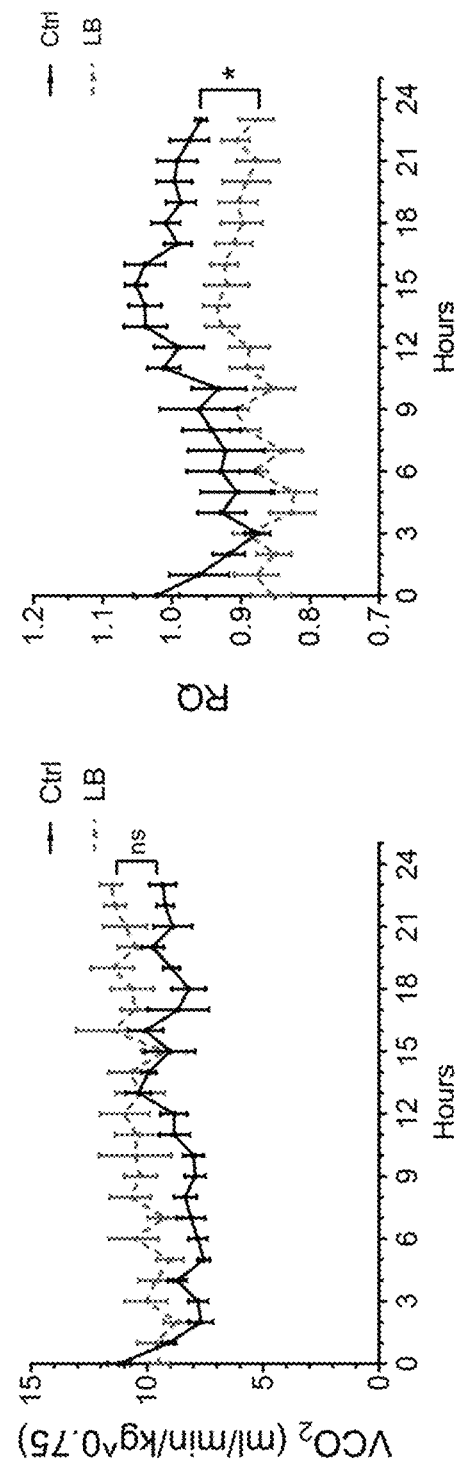
FIG. 9C shows the carbon dioxide exhalation of the mice in the control group and the experimental group with the water extract of *Lycium barbarum*.
FIG. 9D shows the respiratory entropy of the mice in the control group and the experimental group with the water extract of *Lycium barbarum*.

To further validate the enhanced oxidative capacity in the mice from LB group, the inventors measured energy influx and consumption in the whole bodies of both control and LB group mice with metabolic-chamber analysis. The mice in LB group had a significant overall increase in $O_2$ consumption (FIG. 9A), and energy expenditure (EE) (FIG. 9B), suggesting that LB increased the energy expenditure in mice under normal physiological conditions. But there is no significant difference of $CO_2$ production between control and LB group (FIG. 9C), with corresponding a decrease in respiration quotient (RQ) in LB group (FIG. 9D). These data indicate the mice in LB group had an increase in oxidative respiration and was more likely to generate energy using fat. These results were correlated with increased oxidative fiber type.

Figure 10A:
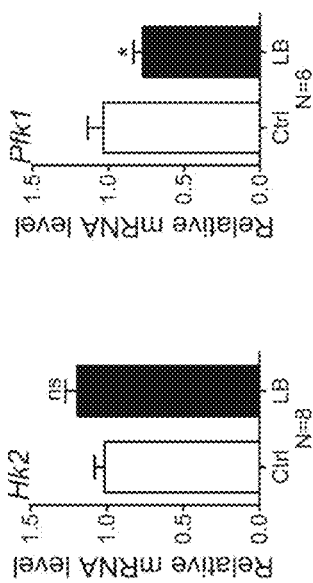
FIG. 10A shows the expression levels of cell glycolysis related gene Hk2 in the myotubes treated with the water extract of *Lycium barbarum* and those in the control group.
Figure 10B:
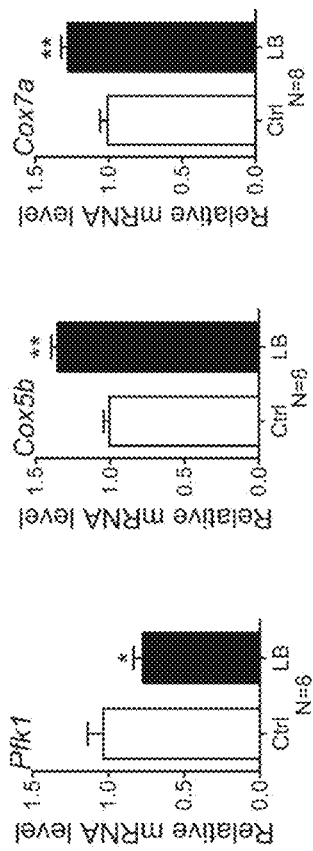
FIG. 10B shows the expression levels of cell glycolysis related gene Pfk1 in the myotubes treated with the water extract of *Lycium barbarum* and those in the control group.
Figure 10C:
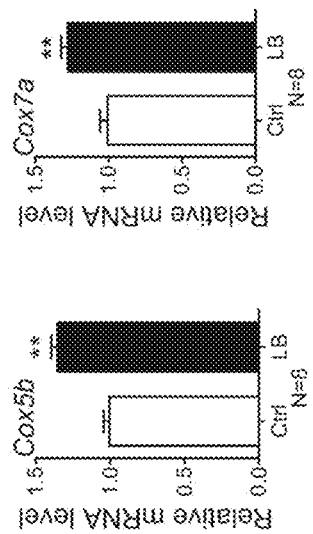
FIG. 10C shows the expression levels of aerobic metabolism related gene Cox5b in the myotubes treated with the water extract of *Lycium barbarum* and those in the control group.
Figure 10D:
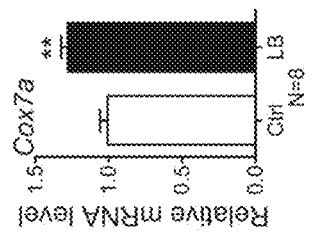
FIG. 10D shows the expression levels of aerobic metabolism related gene Cox7a in the myotubes treated with the water extract of *Lycium barbarum* and those in the control group.
Figure 10E:
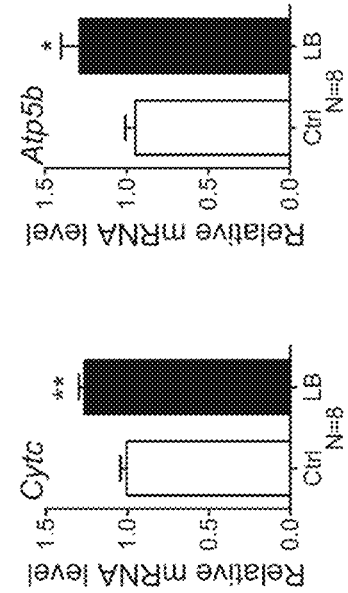
FIG. 10E shows the expression levels of aerobic metabolism related gene Cytc in the myotubes treated with the water extract of *Lycium barbarum* and those in the control group.
Figure 10F:
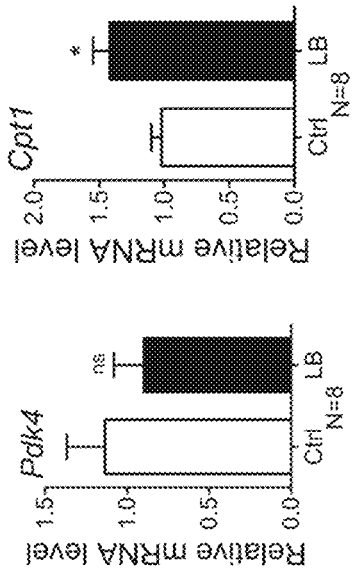
FIG. 10F shows the expression levels of aerobic metabolism related gene Atp5b in the myotubes treated with the water extract of *Lycium barbarum* and those in the control group.
Figure 10G:
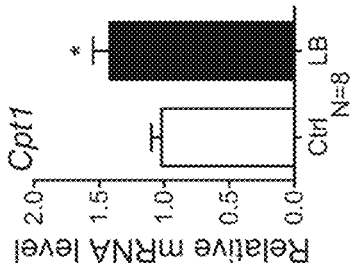
FIG. 10G shows the expression levels of aerobic metabolism related gene Pdk4 in the myotubes treated with the water extract of *Lycium barbarum* and those in the control group.
Figure 10H:
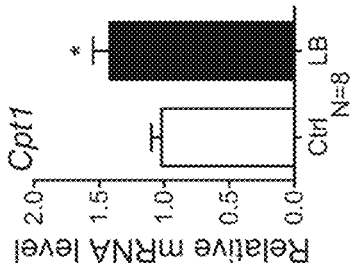
FIG. 10H shows the expression levels of aerobic metabolism related gene Cpt1 in the myotubes treated with the water extract of *Lycium barbarum* and those in the control group.

Next, the levels of key genes about energy production in skeletal muscles were detected. LB decreased the expression of Pfk1, and had no obvious effect on Hk2 expression in TA muscles, which are two key enzymes in glycolysis (FIGS. 10A-10B). Meanwhile, LB up-regulated the level of aerobic metabolism related gene Cox5b, Cox7a (Cytochrome c oxidase subunits) and Cytc (Cytochrome C), suggesting that aerobic metabolism was induced by LB (FIGS. 10C-10E). Increased Atp5b (ATP synthetase 5b) level indicated ATP level was induced by LB (FIG. 10F). The inventors found that LB treatment didn't change the expression of pyruvate dehydrogenase kinase 4 (Pdk4), showing that the increase of ATP synthesis is not realized by the increase of glucose and protein decomposition (FIG. 10G). Fatty acid oxidation related gene cpt1 was significantly induced by LB in TA muscles, indicating that LB increases ATP by promoting fatty acid metabolism (FIG. 10H). These data also support that the TA muscle of the mice in LB group have a higher oxidative capacity than the control group.

Experimental Example 5: LB Promoted Aerobic Respiration in C2C12 Myoblasts

Figure 11C:
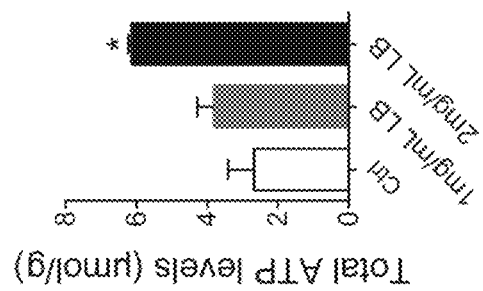
FIG. 11C shows the changes in total ATP levels of myoblasts treated with aqueous extracts of *Lycium barbarum* and myoblasts in the control group.
Figure 11B:
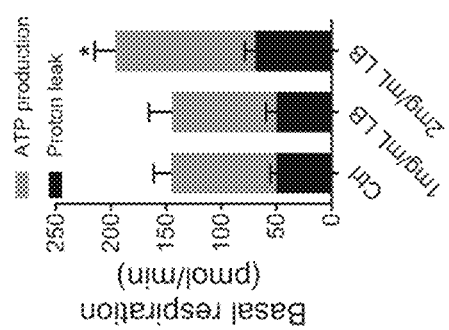
FIG. 11B shows the changes in basal respiration of myoblasts treated with aqueous extracts of *Lycium barbarum* and myoblasts in the control group.
Figure 11A:
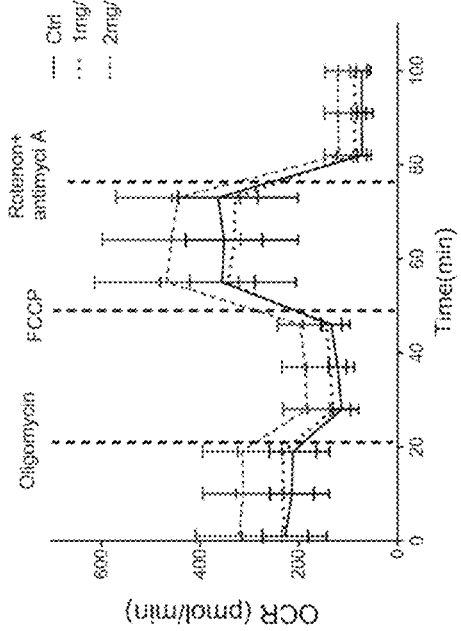
FIG. 11A shows the changes in oxygen consumption rates (OCRs) of myoblasts treated with aqueous extracts of *Lycium barbarum* and myoblasts in the control group.
Figure 11G:
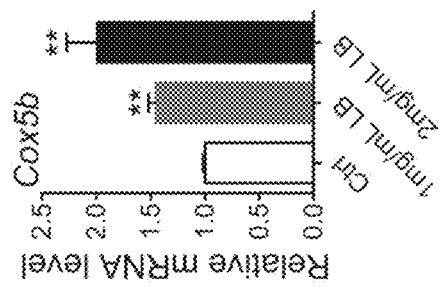
FIG. 11G shows the expression levels of aerobic metabolism related gene Cox5b in myoblasts treated with aqueous extracts of *Lycium barbarum* and myoblasts in the control group.
Figure 11F:
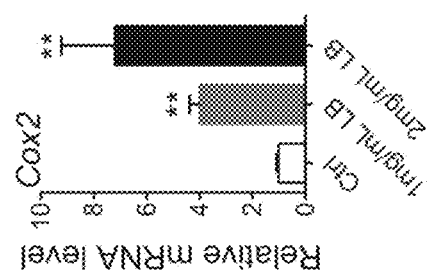
FIG. 11F shows the expression levels of aerobic metabolism related gene Cox2 in myoblasts treated with aqueous extracts of *Lycium barbarum* and myoblasts in the control group.
Figure 11E:
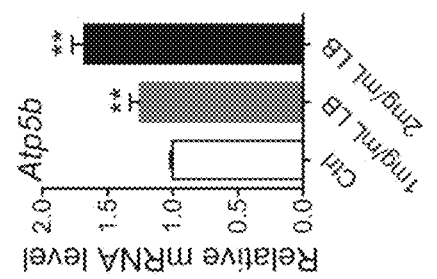
FIG. 11E shows the expression levels of aerobic metabolism related gene Atp5b in myoblasts treated with aqueous extracts of *Lycium barbarum* and myoblasts in the control group.
Figure 11D:
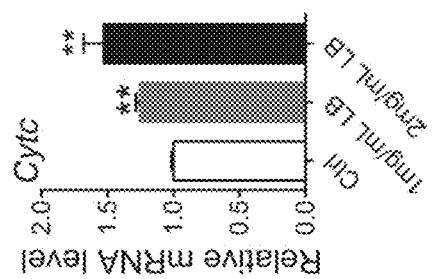
FIG. 11D shows the expression levels of aerobic metabolism related gene Cytc in myoblasts treated with aqueous extracts of *Lycium barbarum* and myoblasts in the control group.

To further assess the effect of LB extract on mitochondrial function in C2C12 myoblasts, cellular bioenergetic profile was analyzed using a Seahorse XF24 Analyzer. As shown in FIG. 11A, 2 mg/mL of LB treated myoblasts had an increase in oxygen consumption rate (OCR) (FIGS. 11A-11B). The increased basal respiration resulted from an elevation in proton leak and mitochondrial ATP generation (FIG. 11C), suggesting that LB promoted both heat production and ATP production.

Figure 12C:
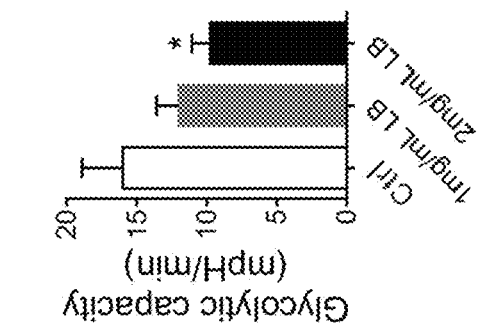
FIG. 12C shows the changes in glycolytic capacity (maximal ECAR) of myoblasts treated with aqueous extracts of *Lycium barbarum* and myoblasts in the control group.
Figure 12B:
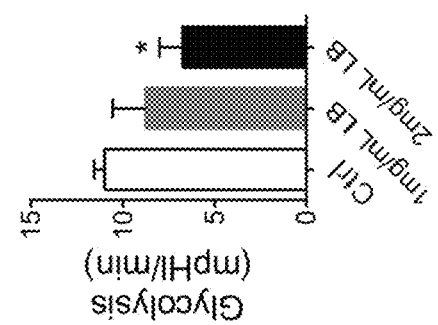
FIG. 12B shows the changes in basal glycolysis level of myoblasts treated with aqueous extracts of *Lycium barbarum* and myoblasts in the control group.
Figure 12A:
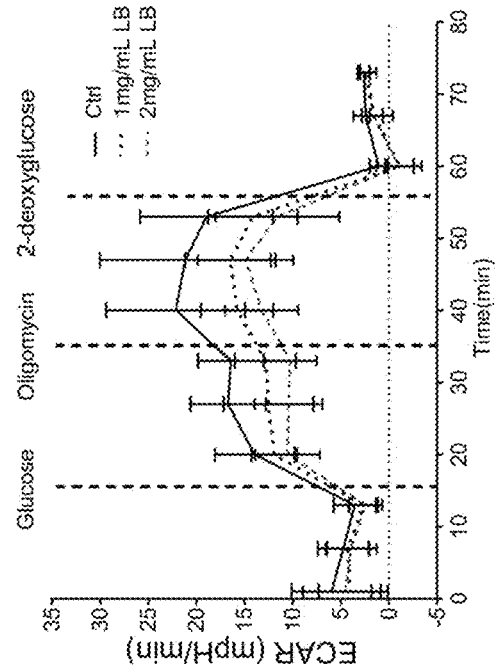
FIG. 12A shows the changes in the extracellular acidification rate (ECAR) of myoblasts treated with aqueous extracts of *Lycium barbarum* and myoblasts in the control group.
Figure 12E:
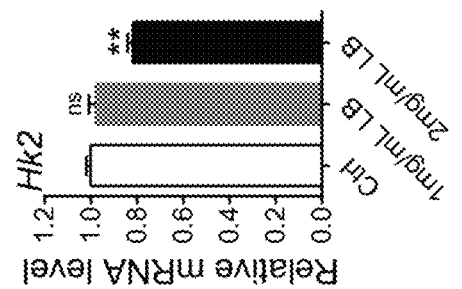
FIG. 12E shows the expression levels of cell glycolysis related gene Hk2 of myoblasts treated with aqueous extracts of *Lycium barbarum* and myoblasts in the control group.
Figure 12D:
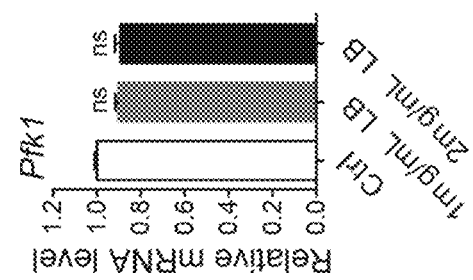
FIG. 12D shows the expression levels of cell glycolysis related gene Pfk1 of myoblasts treated with aqueous extracts of *Lycium barbarum* and myoblasts in the control group.

Furthermore, after addition of an uncoupler carbonyl cyanide-4-(trifluoromethoxy) phenylhydrazone (FCCP), 2 mg/mL of LB treated myoblasts showed higher maximal respiration and spare respiratory capacity (FIG. 11A), indicating better respiration potential. Consistent with increased ATP generation in C2C12 cells, total ATP level detected using kit was also increased by more than 2 times (FIG. 11C). Meanwhile, the transcriptional levels of the central components of the electron transport chain in mitochondria were measured. LB dose dependently increased the expression of cytochrome c (Cytc), the subunits of cytochrome c oxidase (Cox2 and Cox5b) and ATP synthase (Atp5b) (FIGS. 11D-11G), further supporting the increased ATP generation. Furthermore, LB treated myoblasts exhibited a lower extracellular acidification rate (ECAR) as measured by a Seahorse XF24 Analyzer, indicating decreased glycolytic flux and attenuated glycolytic capacity (FIGS. 12A-12C). Consistent with the decreased glycolytic flux, LB treated myoblasts showed lower mRNA level of hexokinase 2 (Hk2), a key enzyme in the first step in glucose metabolism pathways, with no change of the level of phosphofructokinase 1 (Pfk1) (FIGS. 12D-12E). Therefore, LB promoted aerobic respiration and inhibited glycolysis in C2C12 myoblasts.

Figure 13:
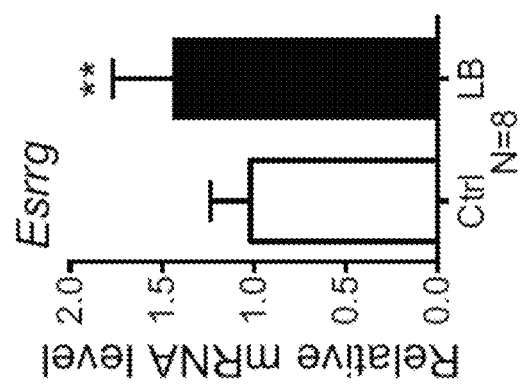
FIG. 13 shows the expression level of ERRγ in the tibialis anterior muscles of the experimental group mice treated with the *Lycium barbarum* water extract and those in the control group mice.
Figure 14:
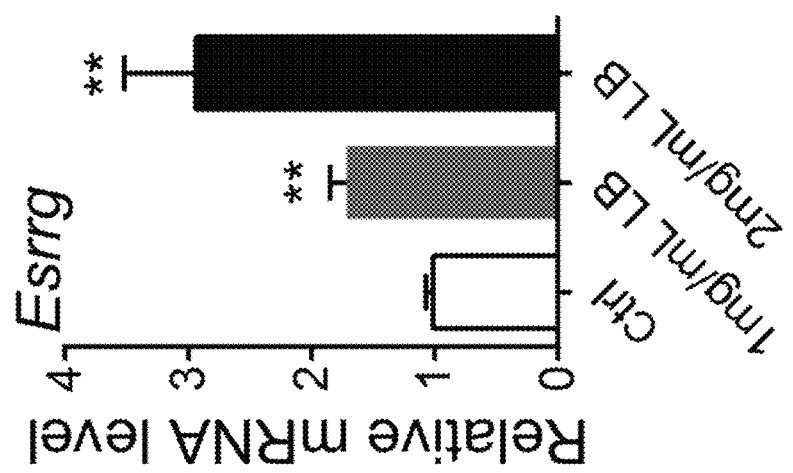
FIG. 14 shows the expression level of ERRγ in myotubes treated with the *Lycium barbarum* water extract and myotubes of the control group.
Figure 15C:
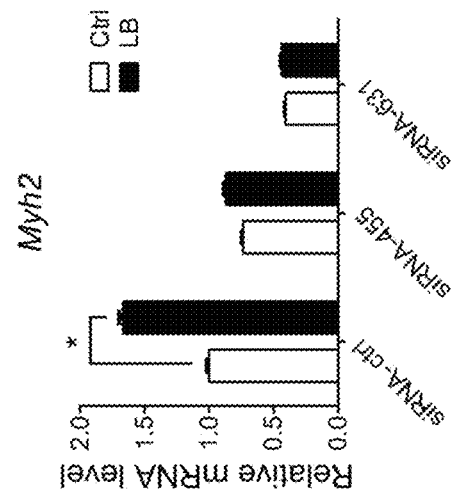
FIG. 15C shows the expression levels of skeletal muscle fiber-related gene Myh2 in myotubes treated with water extract of *Lycium barbarum* and those in the control group after the Esrrg gene was disturbed.
Figure 15B:
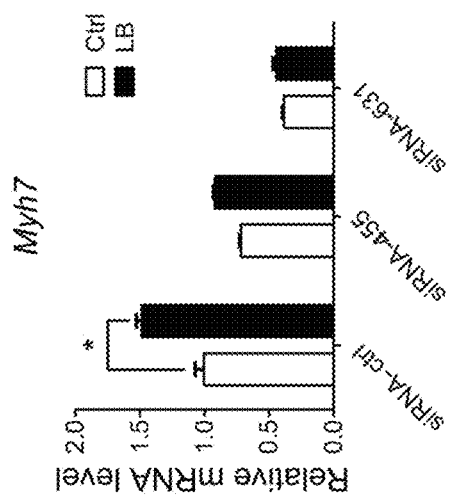
FIG. 15B shows the expression levels of skeletal muscle fiber-related gene Myh7 in myotubes treated with water extract of *Lycium barbarum* and those in the control group after the Esrrg gene was disturbed.
Figure 15A:
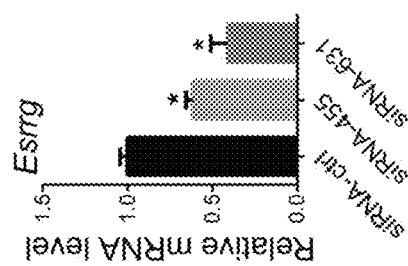
FIG. 15A shows the expression levels of Esrrg in myotubes treated with water extract of *Lycium barbarum* and those in the control group after the Esrrg gene was disturbed.
Figures 15D, 15E, 15F:
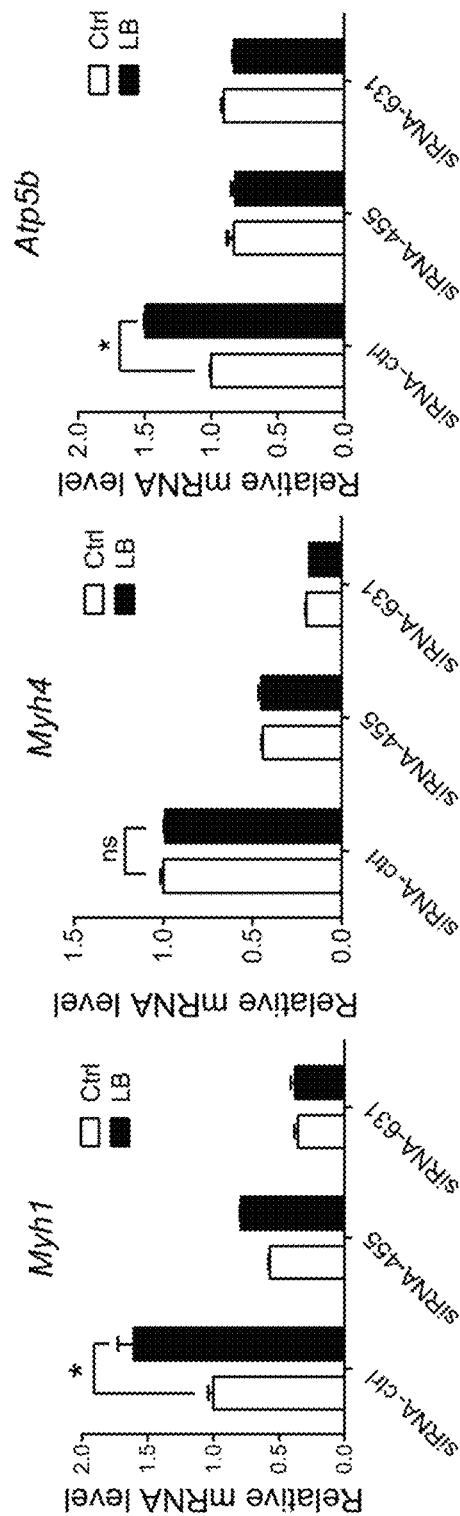
FIG. 15D shows the expression levels of skeletal muscle fiber-related gene Myh1 in myotubes treated with water extract of *Lycium barbarum* and those in the control group after the Esrrg gene was disturbed.
FIG. 15E shows the expression levels of skeletal muscle fiber-related gene Myh4 in myotubes treated with water extract of *Lycium barbarum* and those in the control group after the Esrrg gene was disturbed.
FIG. 15F shows the expression levels of Atp5b as a key gene of ATP in myotubes treated with water extract of *Lycium barbarum* and those in the control group after the Esrrg gene was disturbed.
Figure 16A:
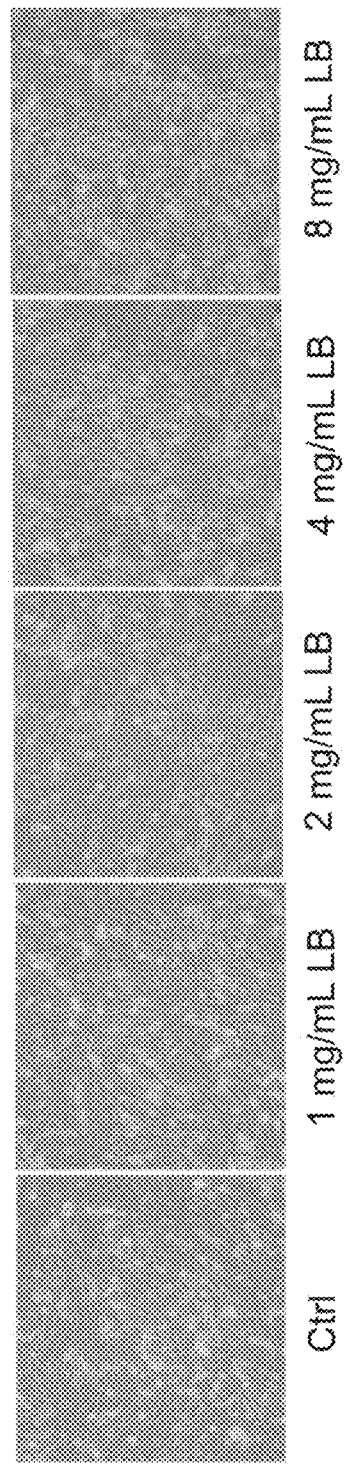
FIG. 16A shows the morphology of the C2C12 myotubes treated with different concentrations (1.0, 2.0, 4.0 and 8.0 mg/mL) of *Lycium barbarum* extract.
Figure 16D:
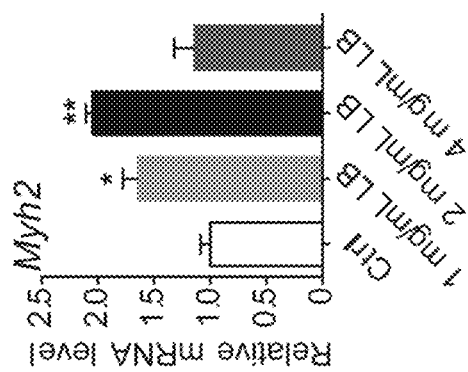
FIG. 16D shows the RNA levels of Myh2 in the C2C12 myotubes treated with different doses of *Lycium barbarum* extract.
Figure 16C:
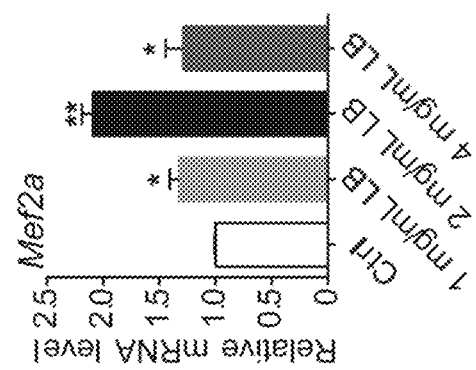
FIG. 16C shows the RNA levels of Mef2a in the C2C12 myotubes treated with different doses of *Lycium barbarum* extract.
Figure 16B:
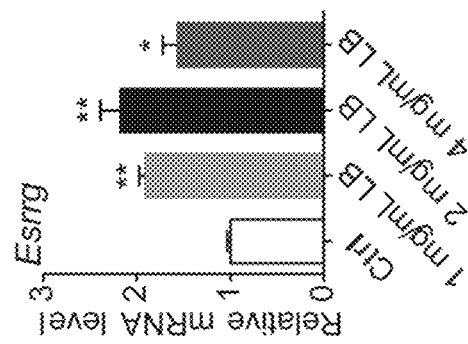
FIG. 16B shows the RNA levels of Esrrg in the C2C12 myotubes treated with different doses of *Lycium barbarum* extract.

Experimental Example 6: LB Modulated Muscle Fiber Type Switch in ERRγ Dependent Manner Next, the inventors investigated the molecular mechanism behind how LB modulated muscle fiber type switch. The inventors first assessed the expression of the known key regulators involved in the metabolic remodeling of skeletal muscle, including AMPK, PGC-1, Sirt1 and PPAR. The inventors found LB increase the transcriptional level of Esrrg both in vitro and in vivo (FIGS. 13-14). To confirm that LB modulates muscle fiber type and metabolic type switch by regulating ERR pathway, the expression of Esrrg was knocked down using siRNA in C2C12 myotubes. Deficiency of ERRγ inhibited LB induced the mRNA levels of the markers of oxidative fibers (Myh7, Myh2, and Myh1) and ATP synthase (Atp5b) (FIG. 15A-15F), demonstrating that LB increased the ratio of oxidative fiber types and enhanced the aerobic respiration in an ERRγ dependent manner.

To test whether LB showed hormetic effects, high doses of LB extract were used to treat C2C12 myotubes. The inventors found that when the concentration of LB reached 8 mg/mL, many cells died. Although LB at a concentration of 4 mg/mL also increased the level of the gene (Esrrg and Mef2a) expression, the extent of this upregulation was significantly lower than that induced by the 2 mg/mL extract (FIG. 16A-16D). Therefore, the beneficial function of LB on C2C12 cells is dose-dependent only in a certain concentration range (approximately 0-2 mg/mL, for example, 0.1-2 mg/mL or 0.5-2 mg/mL).

As reported earlier, exercise was considered an effective way to improve muscle mass and function. Endurance exercise increases the muscle mass, reduces the fat mass, promotes fiber type transformation toward the slow-twitch, stimulates mitochondrial biogenesis and fatty acid oxidation, promotes $O_2$ utilization, $CO_2$ and heat production and resulting in a more oxidative phenotype and improved endurance capacity of the muscles. Thus, exercise triggers a metabolic and structural remodeling in skeletal muscle, thus leading to improved skeletal muscle performance. In recent years, some natural compounds defined as "exercise mimetics" was reported to produce metabolic effects similar to those induced by exercise. Although these functional natural compounds cannot fully replace the benefits of exercise, they have the potential to offer at least some of the benefits of exercise. *Lycium barbarum* extract can increase muscle mass, reduce fat mass, promotes fiber type switch, stimulate mitochondrial biogenesis and fatty acid oxidation, promotes $O_2$ utilization, ATP and heat production resulting in a more oxidative phenotype and enhanced endurance of the muscles. So it is extremely useful as an "exercise mimetic".

As a Chinese herbal medicine and functional food, *Lycium barbarum* extract with "exercise mimetic" effect may be applied to many fields. For example, for endurance athletes, *Lycium barbarum* may be beneficial to increase the proportion of oxidative muscle fibers. For people lacking or unable to achieve adequate physical exercise, *Lycium barbarum* extract may be able to prevent muscle loss and promote muscle metabolism to a certain extent. Moreover, loss of skeletal muscle mass is one of the most widespread and deleterious processes in human aging, which compromises the quality of life. Aging muscle atrophy results from atrophy of type II myofibers. In the present disclosure, the inventors found that *Lycium barbarum* can increase the type IIa fibers and the muscle mass. At the same time, mitochondria play a pivotal role in skeletal muscle homeostasis and aging-related defects in mitochondrial energy metabolism have been proposed to be involved in aging muscle atrophy, while the aerobic respiration and energy production was improved by *Lycium barbarum* treatment. Therefore, *Lycium barbarum* extract could maintain functional skeletal muscle mass by up-regulating mitochondrial metabolism and fiber-type transformation, and it may contribute to ameliorate aging muscle atrophy.

Although the subject matter has been described in terms of exemplary embodiments, it is not limited thereto. Rather, the appended claims should be construed broadly, to include other variants and embodiments, which may be made by those skilled in the art.

What is claimed is:

1. A composition for promoting skeletal muscle oxidative muscle fiber generation, comprising a *Lycium barbarum* extract, wherein the *Lycium barbarum* extract comprises polysaccharide, *Lycium barbarum* flavone, carotenoid, polyphenol, and *Lycium barbarum* pigment,
   wherein in the *Lycium barbarum* extract, polysaccharide is present in a range of from about 10.0 wt. % to about 70.0 wt. %, *Lycium barbarum* flavone is present in a range of from about 0.1 wt. % to about 5.0 wt. %, carotenoid is present in a range of from about 0.1 wt. % to about 3.0 wt. %, polyphenol is present in a range of from about 0.1 wt. % to about 8.0 wt. %, and *Lycium barbarum* pigment is present in a range of from about 0.1 wt. % to about 8.0 wt. %, based on a total dry weight of the extract in a dry powder form,
   wherein the *Lycium barbarum* extract is in a powder form.

2. The composition of claim 1, further comprising one or more excipients selected from the group consisting of a solvent, a co-solvent, an emulsifier, a preservative, a buffer, a protein powder, and any combination thereof.

3. The composition of claim 1, wherein the composition is in a form of a powdered drink configured for making a drink in liquid form.

4. The composition of claim 3, wherein the drink in liquid form is a sports drink.

5. The composition of claim 1, wherein in the *Lycium barbarum* extract, polysaccharide is present in a range of from about 50.0 wt. % to about 70.0 wt. % based on the total dry weight of the extract in a dry powder form.

6. The composition of claim 1, wherein the composition comprises two or more types of polysaccharides, two or more types of *Lycium barbarum* flavones, two or more types of carotenoids, two or more polyphenols, or two or more types of *Lycium barbarum* pigments.

7. The composition of claim 1, wherein the composition is a pharmaceutical composition, a functional composition, a type of food, or a dietary supplement.

8. A method of making the composition of claim 1, comprising steps of making a *Lycium barbarum* extract, the steps of making the *Lycium barbarum* extract including steps of:
   soaking dried *Lycium barbarum* berries in water;
   crushing the *Lycium barbarum* berries to provide a soaked berry powder;
   decocting the soaked berry powder in boiling water twice to obtain a decoction;
   distilling the decoction under vacuum after a filtration to obtain a concentrate; and
   lyophilizing the concentrate to obtain a dry powder as the *Lycium barbarum* extract.

9. The method of claim 8, further comprising formulating the composition by adding one or more ingredients into the *Lycium barbarum* extract.

10. The method of claim 8, further comprising the one or more ingredients are selected from the group consisting of a solvent, a co-solvent, an emulsifier, a preservative, a buffer, a protein powder, and any combination thereof.

11. The method of claim 8, wherein the composition is for making a drink in liquid form.

12. The method of claim 9, further comprising dissolving the *Lycium barbarum* extract in water to obtain an aqueous liquid.

13. A method for increasing the weight of skeletal muscle, and/or increasing the proportion of skeletal muscle oxidative muscle fibers, said method comprising administering a suitable amount of the composition of claim 1 into a human subject in need thereof.

14. A method for improving the level of aerobic metabolism, and/or reducing glycolysis level, said method comprising administering a suitable amount of the composition of claim 1 into a human subject in need thereof.

15. A method for increasing the content of myoglobin, said method comprising administering a suitable amount of the composition of claim 1 into a human subject in need thereof.

16. A method for improving exercise endurance, and/or combating sports fatigue, and/or in exercise simulation, said method comprising administering a suitable amount of the composition of claim 1 into a human subject.

17. A method for activating the ERRγ pathway, and/or regulating muscle fiber types by activating the ERRγ pathway, said method comprising administering a suitable amount of the composition of claim 1 into a human subject.

\* \* \* \* \*